(12) United States Patent
Sakurada et al.

(10) Patent No.: US 12,084,274 B2
(45) Date of Patent: Sep. 10, 2024

(54) METHOD, CONTROL DEVICE, AND SYSTEM

(71) Applicant: TOYOTA JIDOSHA KABUSHIKI KAISHA, Toyota (JP)

(72) Inventors: Shin Sakurada, Toyota (JP); Kazuya Nishimura, Anjo (JP); Soutaro Kaneko, Nagoya (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 222 days.

(21) Appl. No.: 17/712,591

(22) Filed: Apr. 4, 2022

(65) Prior Publication Data

US 2022/0341908 A1  Oct. 27, 2022

(30) Foreign Application Priority Data

Apr. 22, 2021  (JP) .................... 2021-072737

(51) Int. Cl.
| | |
|---|---|
| *B65F 3/00* | (2006.01) |
| *B64C 39/02* | (2023.01) |
| *G01N 33/00* | (2006.01) |
| *B64U 101/00* | (2023.01) |
| *B65F 9/00* | (2006.01) |
| *G05D 105/00* | (2024.01) |
| *G05D 105/28* | (2024.01) |

(52) U.S. Cl.
CPC ............ *B65F 3/00* (2013.01); *B64C 39/024* (2013.01); *G01N 33/0075* (2013.01); *B64U 2101/00* (2023.01); *B64U 2201/10* (2023.01); *B65F 9/00* (2013.01); *G05D 2105/14* (2024.01); *G05D 2105/29* (2024.01)

(58) Field of Classification Search
None
See application file for complete search history.

(56) References Cited

U.S. PATENT DOCUMENTS

| | | | |
|---|---|---|---|
| 5,489,898 A | | 2/1996 | Shigekusa et al. |
| 2018/0074496 A1 | | 3/2018 | Gordon et al. |
| 2018/0075417 A1 | * | 3/2018 | Gordon ................ B64D 1/22 |
| 2020/0082354 A1 | * | 3/2020 | Kurani ................. G01K 1/026 |

FOREIGN PATENT DOCUMENTS

| | | |
|---|---|---|
| CN | 109324552 A | 2/2019 |
| CN | 112389911 A | 2/2021 |
| JP | H06-282792 A | 10/1994 |
| JP | 2003-089427 A | 3/2003 |

* cited by examiner

*Primary Examiner* — Peter D Nolan
*Assistant Examiner* — Michael F Whalen
(74) *Attorney, Agent, or Firm* — Oliff PLC

(57) ABSTRACT

A method executed by a control device includes: acquiring odor information indicating an odor intensity of each of a plurality of garbage collection sites, the odor intensity being detected by an odor sensor; determining an order in which garbage is collected from each of the garbage collection sites based on the odor information; and causing a garbage collection device to sequentially collect the garbage from each of the garbage collection sites according to the order.

14 Claims, 4 Drawing Sheets

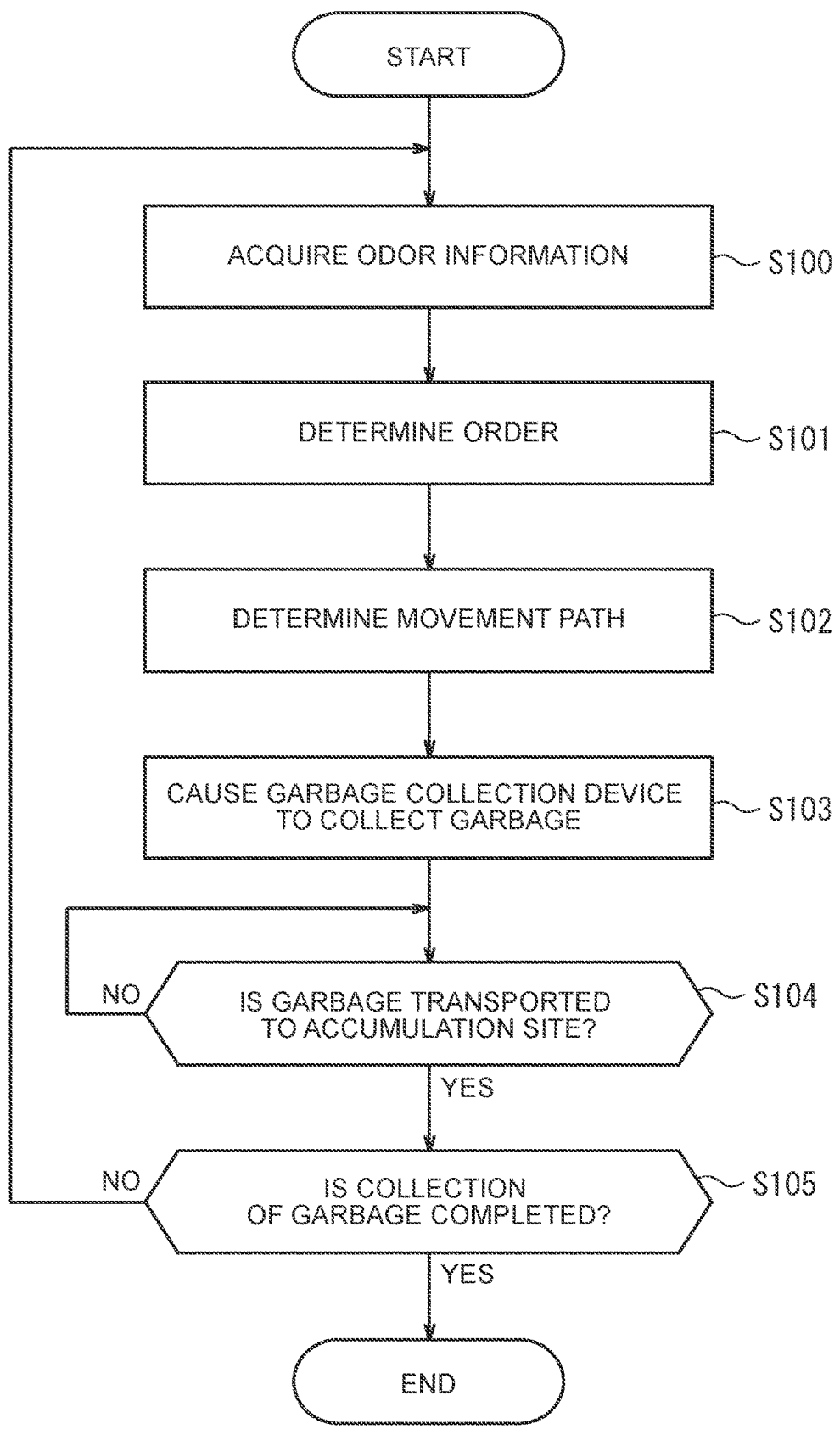

METHOD, CONTROL DEVICE, AND SYSTEM

CROSS-REFERENCE TO RELATED APPLICATION

This application claims priority to Japanese Patent Application No. 2021-072737 filed on Apr. 22, 2021, incorporated herein by reference in its entirety.

BACKGROUND

1. Technical Field

The present disclosure relates to a method, a control device, and a system.

2. Description of Related Art

Conventionally, a technique for collecting garbage using a garbage collection device such as a garbage collection vehicle is known. For example, Japanese Unexamined Patent Application Publication No. 6-282792 (JP 6-282792 A) discloses a system for confirming patrol progress of a garbage collection vehicle that patrols a plurality of garbage accumulation sites.

SUMMARY

There is room for improvement in a technique for collecting garbage using a garbage collection device.

An object of the present disclosure made in view of such circumstances is to improve a technique for collecting garbage using a garbage collection device.

A method according to one embodiment of the present disclosure is a method executed by a control device, the method including acquiring odor information indicating an odor intensity of each of a plurality of garbage collection sites, the odor intensity being detected by an odor sensor, determining an order in which garbage is collected from each of the garbage collection sites based on the odor information, and causing a garbage collection device to sequentially collect the garbage from each of the garbage collection sites according to the order.

The control device according to the one embodiment of the present disclosure is a control device including a control unit, in which the control unit acquires odor information indicating an odor intensity of each of a plurality of garbage collection sites, the odor intensity being detected by an odor sensor, the control unit determines an order in which garbage is collected from each of the garbage collection sites based on the odor information, and the control unit causes a garbage collection device to sequentially collect the garbage from each of the garbage collection sites according to the order.

A system according to the one embodiment of the present disclosure is a system including a control device and a garbage collection device that communicates with the control device, in which the control device acquires odor information indicating an odor intensity of each of a plurality of garbage collection sites, the odor intensity being detected by an odor sensor, the control device determines an order in which garbage is collected from each of the garbage collection sites based on the odor information, and the garbage collection device sequentially collects the garbage from each of the garbage collection sites according to the order.

According to the one embodiment of the present disclosure, a technique for collecting garbage using a garbage collection device is improved.

BRIEF DESCRIPTION OF THE DRAWINGS

Features, advantages, and technical and industrial significance of exemplary embodiments of the present disclosure will be described below with reference to the accompanying drawings, in which like signs denote like elements, and wherein:

FIG. 4 is a flowchart showing operation of the control device.

DETAILED DESCRIPTION OF EMBODIMENTS

Hereinafter, an embodiment of the present disclosure will be described.

Outline of Embodiment

Figure 1:
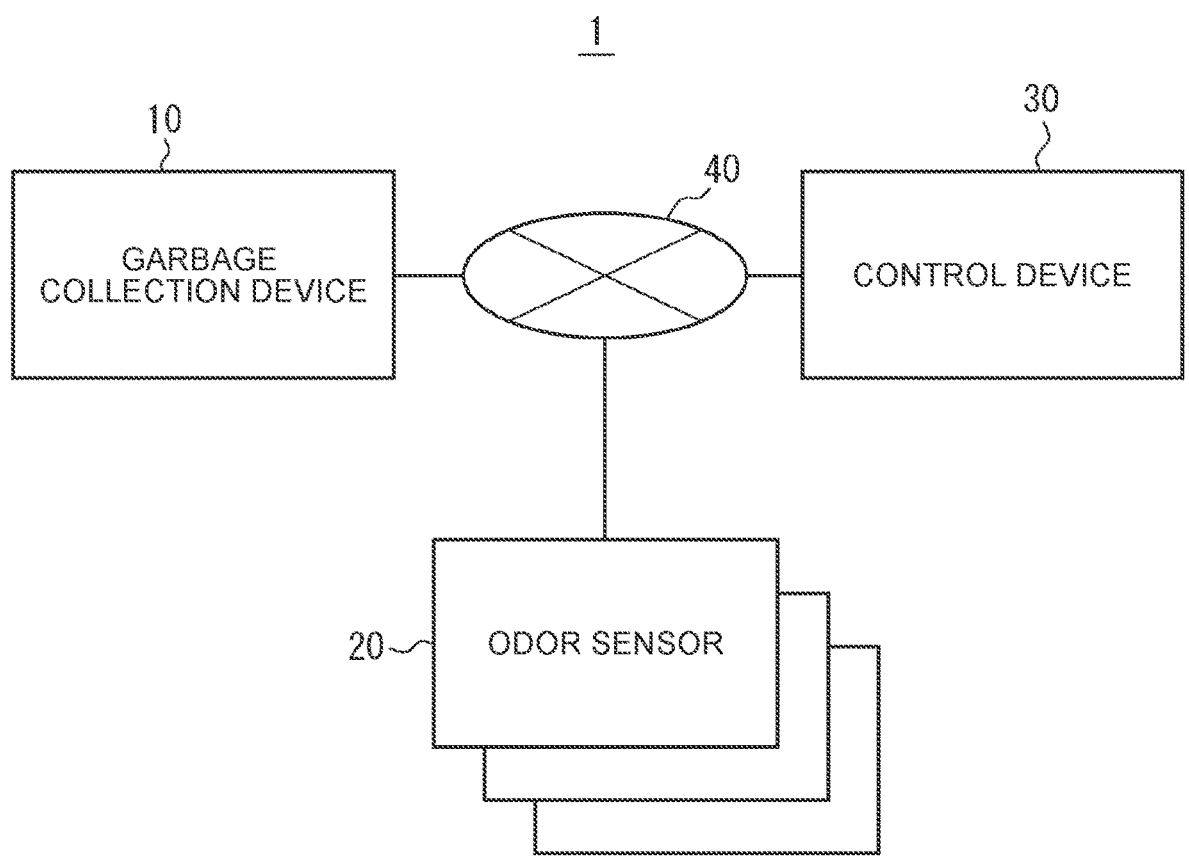
FIG. 1 is a block diagram showing a schematic configuration of a system according to an embodiment of the present disclosure.

The outline of a system 1 according to the embodiment of the present disclosure will be described with reference to FIG. 1. The system 1 includes a garbage collection device 10, a plurality of odor sensors 20, and a control device 30. The control device 30 can communicate with the garbage collection device 10 and each odor sensor 20 via a network 40 including, for example, the Internet and a mobile communication network.

The garbage collection device 10 is a device that collects garbage from a plurality of garbage collection sites and transports the garbage to an accumulation site. In the present embodiment, the garbage collection device 10 is an unmanned aerial vehicle such as a drone. The garbage collection device 10 may include any mechanical structure that holds garbage, such as a hook or a robot arm. The garbage collection device 10 operates autonomously or in cooperation with the control device 30. For example, the garbage collection device 10 may be able to fly along a movement path instructed by the control device 30. Further, when an obstacle is detected using a sensor such as a camera, the garbage collection device 10 may be able to autonomously bypass the obstacle. Further, when garbage placed in the garbage collection site is detected using a sensor such as a camera, the garbage collection device 10 may be able to autonomously collect the garbage.

Each of the garbage collection sites is provided on each balcony of a building such as a complex housing. For example, a user who is a resident of the complex housing puts garbage to be collected in a garbage collection site on the balcony. The accumulation site is provided in the building and is a site where the garbage collected from each garbage collection site by the garbage collection device 10 is temporarily accumulated. The garbage accumulated in the accumulation site is collected by, for example, a garbage collection vehicle, and transported to a garbage disposal site. The garbage collection device 10 according to the present embodiment can communicate with the control device 30 via the network 40 including, for example, the Internet and the mobile communication network.

The odor sensor 20 has, for example, a sensor element using a semiconductor or a crystal oscillator, and is a sensor that detects an odor intensity of ambient air. In the present embodiment, each of a plurality of the odor sensors 20 is provided in each of the garbage collection sites. Each odor sensor 20 detects the odor intensity of the garbage collection site where the odor sensor 20 is provided. In the present embodiment, the odor sensor 20 can communicate with the control device 30 via the network 40.

The control device 30 is, for example, a computer such as a personal computer (PC), a server, a smartphone, or a tablet terminal.

First, the outline of the present embodiment will be described, and the details will be described later. The control device 30 acquires odor information indicating the odor intensity of each garbage collection site detected by the odor sensor 20. The control device 30 determines the order in which garbage is collected from each garbage collection site based on the odor information. Then, the control device 30 causes the garbage collection device 10 to sequentially collect the garbage from each garbage collection site according to the determined order.

As described above, according to the present embodiment, the order in which the garbage is collected is determined according to the odor intensity of each garbage collection site. Generally, when garbage with a strong odor intensity is left for a long period of time, there is a high possibility that users around such a garbage collection site feel uncomfortable. According to the present embodiment, a technique for collecting the garbage using the garbage collection device is improved in that the garbage is collected in the order in which the odor intensity of each garbage collection site is considered, for example, the garbage is collected in the order from a garbage collection site with a strong odor intensity, which leads to reduce a possibility that users feel uncomfortable.

Next, configurations in the system 1 will be described in detail.

Configuration of Garbage Collection Device

Figure 2:
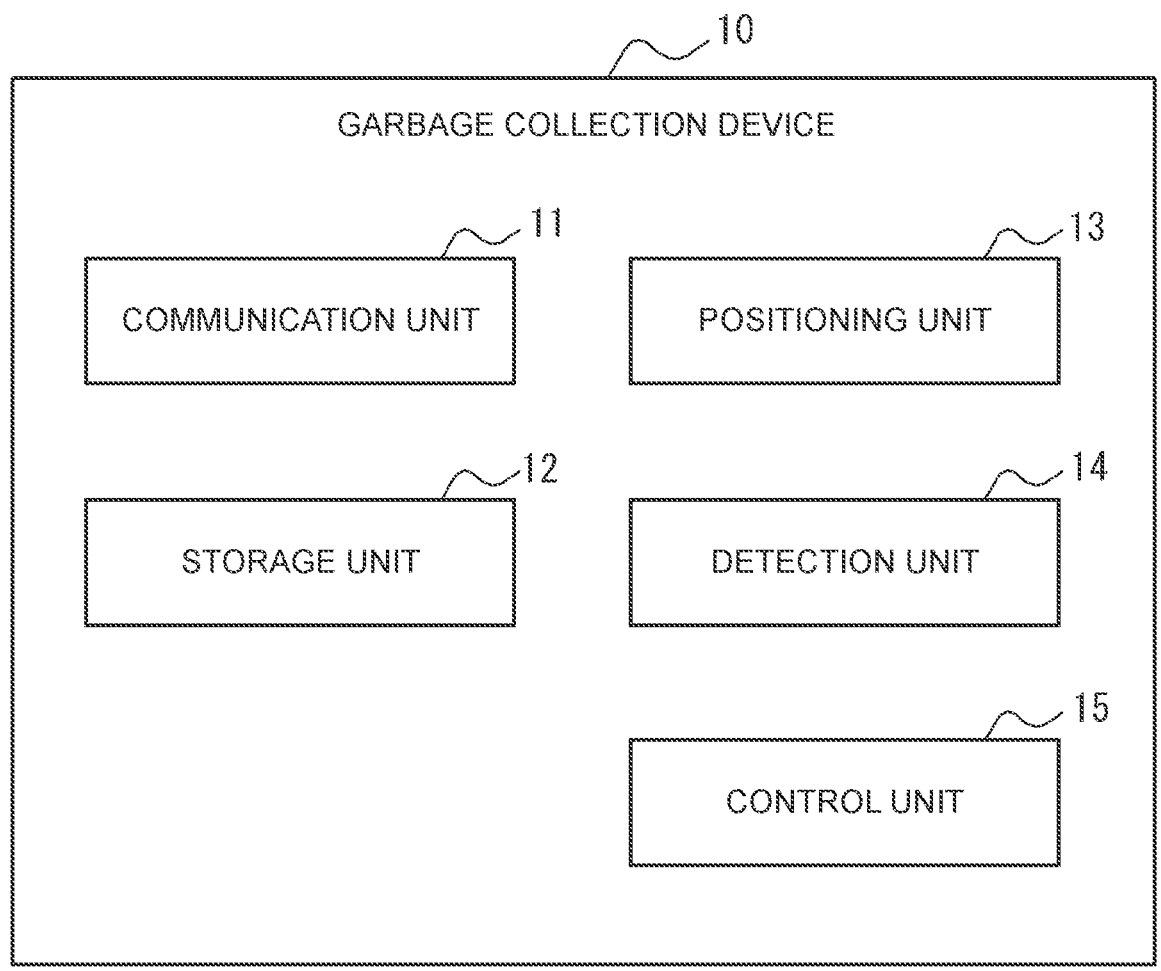
FIG. 2 is a block diagram showing a schematic configuration of a garbage collection device.

As shown in FIG. 2, the garbage collection device 10 includes a communication unit 11, a storage unit 12, a positioning unit 13, a detection unit 14, and a control unit 15.

The communication unit 11 includes one or more communication interfaces connected to the network 40. The communication interface supports, for example, 4th generation (4G) and 5th generation (5G) mobile communication standards. The supported standards are not limited to these, and the communication interface may support any mobile communication standards. In the present embodiment, the garbage collection device 10 communicates with the control device 30 via the communication unit 11.

The storage unit 12 includes one or more memories. The memories are, for example, a semiconductor memory, a magnetic memory, or an optical memory, but are not limited to these memories. Each memory included in the storage unit 12 may function as, for example, a main storage device, an auxiliary storage device, or a cache memory. The storage unit 12 stores any information used for the operation of the garbage collection device 10. For example, the storage unit 12 may store a system program, an application program, and embedded software. The information stored in the storage unit 12 may be updatable with information received from the network 40 via the communication unit 11, for example.

The positioning unit 13 includes a receiver compatible with a satellite positioning system. The receiver is compatible with, for example, the Global Positioning System (GPS), but the compatible satellite positioning system is not limited to this, and the receiver may be compatible with any satellite positioning system. The positioning unit 13 also includes, for example, a gyro sensor, a geomagnetic sensor, and a barometric pressure sensor. The garbage collection device 10 according to the present embodiment can acquire position information and posture information on the garbage collection device 10 itself using the positioning unit 13. The position information may include two-dimensional coordinate data including latitude and longitude, and may include three-dimensional coordinate data including altitude in addition to latitude and longitude. The posture information can include information indicating an orientation of the garbage collection device 10 itself and an inclination thereof, but is not limited to this, and may include any information on a posture of the garbage collection device 10 itself.

The detection unit 14 includes one or more sensors used for detecting obstacles existing around the garbage collection device 10. In the present embodiment, the sensors include, but are not limited to, a camera, and may further include, for example, a millimeter wave radar or light detection and ranging (LiDAR). The output information of the sensors of the detection unit 14 can be used, for example, for the garbage collection device 10 to fly while autonomously bypassing obstacles around the garbage collection device 10.

The control unit 15 includes one or more processors, one or more programmable circuits, one or more dedicated circuits, or a combination of these. The processors are, for example, a general-purpose processor such as a central processing unit (CPU) or a graphics processing unit (GPU), or a dedicated processor specialized for a specific process, but are not limited to these processors. The programmable circuits are, for example, a field-programmable gate array (FPGA), but are not limited to the circuit. The dedicated circuits are, for example, an application specific integrated circuit (ASIC), but are not limited to the circuit. The control unit 15 controls the operation of the entire garbage collection device 10.

Configuration of Control Device

Figure 3:
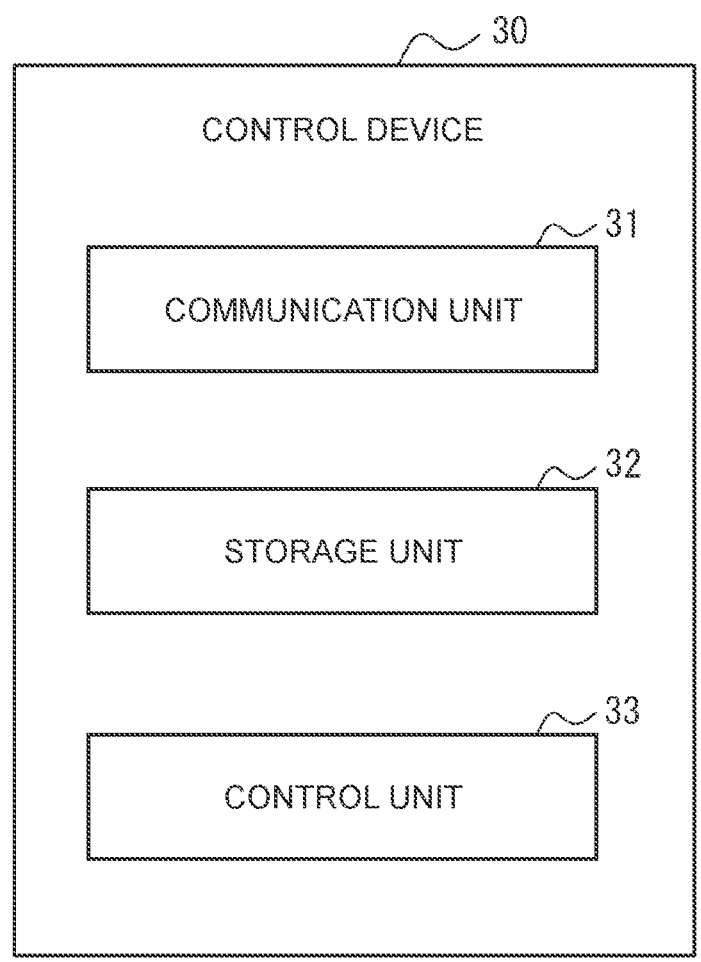
FIG. 3 is a block diagram showing a schematic configuration of a control device.

As shown in FIG. 3, the control device 30 includes a communication unit 31, a storage unit 32, and a control unit 33.

The communication unit 31 includes one or more communication interfaces connected to the network 40. The communication interfaces support, for example, a mobile communication standard, a wired local area network (LAN) standard, or a wireless LAN standard, but the supported standards are not limited to these, and the communication interfaces may support any communication standard. In the present embodiment, the control device 30 communicates with the garbage collection device 10 via the communication unit 31.

The storage unit 32 includes one or more memories. Each memory included in the storage unit 32 may function as, for example, a main storage device, an auxiliary storage device, or a cache memory. The storage unit 32 stores any information used for the operation of the control device 30. For example, the storage unit 32 may store a system program, an application program, a database, and map information. The information stored in the storage unit 32 may be updatable with information received from the network 40 via the communication unit 31, for example.

In the present embodiment, the storage unit 32 stores information on a building including the garbage collection sites and the accumulation site. The information on the building includes any information used for determining a movement path along which the garbage collection device 10 moves to any position in the building. For example, the information on the building may include three-dimensional survey data of the building and three-dimensional coordinate data of each garbage collection site and the accumulation site provided in the building. The three-dimensional survey data of the building is, for example, a plurality of three-dimensional coordinate data (that is, three-dimensional point cloud data) corresponding to the building. By using the three-dimensional survey data of the building, the control device 30 can determine the movement path of the garbage collection device 10 such that the garbage collection device 10 does not contact an outer wall of the building, for example.

The control unit 33 includes one or more processors, one or more programmable circuits, one or more dedicated circuits, or a combination of these. The control unit 33 controls the operation of the entire control device 30. Details of the operation of the control device 30 controlled by the control unit 33 will be described later.

Operation Flow of Control Device

The operation of the control device 30 according to the present embodiment will be described with reference to FIG. 4.

Step S100: The control unit 33 of the control device 30 acquires odor information indicating the odor intensity of each garbage collection site detected by the odor sensor 20.

Specifically, the control unit 33 acquires information indicating the odor intensity of each garbage collection site as odor information from the odor sensors 20 via the communication unit 31 and the network 40. Each odor sensor 20 may detect the odor intensity and notify the control device 30 of the odor intensity at a predetermined cycle, for example. Alternatively, the control unit 33 may transmit a request signal to each odor sensor 20 via the communication unit 31 and the network 40, and every time each odor sensor 20 receives the request signal, each odor sensor 20 may detect the odor intensity and notify the control device 30 of the odor intensity.

Step S101: The control unit 33 determines the order in which garbage is collected from each garbage collection site based on the odor information acquired in step S100.

Any method can be adopted for determining the order based on the odor information. In one example, the control unit 33 may determine the order in which garbage is collected from each garbage collection site such that the stronger the odor intensity, the earlier the garbage is collected. In another example, the control unit 33 may determine the order in which garbage is collected from each garbage collection site based on the odor intensity in the future of each garbage collection site, the odor intensity being estimated based on the odor information. Specifically, the control unit 33 estimates a chronological change of the odor intensity of each garbage collection site. The control unit 33 may determine the order in which garbage is collected from each garbage collection site such that a sum of values obtained by integrating the odor intensity from the current time to a time at which the garbage collection device 10 collects garbage in each garbage collection site is minimized. In other words, the control unit 33 may determine the order in which the sum of the integral values of the odor intensity is minimized by solving the optimization problem for a plurality of patterns in which the order of collecting the garbage is changed.

Step S102: The control unit 33 determines the movement path of the garbage collection device 10 for sequentially collecting the garbage from each garbage collection site according to the order determined in step S101.

Specifically, the control unit 33 determines the movement path of the garbage collection device 10 for sequentially collecting the garbage from each garbage collection site according to the above order using the information on the building stored in the storage unit 32. Here, the control unit 33 may determine the movement path along which the garbage collection device 10 transports the garbage to the accumulation site every time the garbage collection device 10 collects the garbage from a predetermined number (for example, one) of the garbage collection sites. Alternatively, the control unit 33 may determine the movement path along which the garbage collection device 10 transports the garbage to the accumulation site after collecting the garbage from all the garbage collection sites.

Step S103: The control unit 33 causes the garbage collection device 10 to sequentially collect the garbage from each garbage collection site according to the order determined in step S101 and the movement path determined in step S102.

Specifically, the control unit 33 notifies the garbage collection device 10 of the determined order and the determined movement path via the communication unit 31 and the network 40. The garbage collection device 10 sequentially collects the garbage from each garbage collection site according to the notified order and the notified movement path. Here, when the weight of the collected garbage is equal to or more than the specified amount, for example, the garbage collection device 10 may transport the garbage to the accumulation site irrespective of the notified movement path.

Step S104: The control unit 33 determines whether the garbage collected from at least one of the garbage collection sites by the garbage collection device 10 is transported to the accumulation site. When the control unit 33 determines that the garbage is transported to the accumulation site (step S104—Yes), the process proceeds to step S105. On the other hand, when the control unit 33 determines that the garbage is not transported to the accumulation site (step S104—No), the process repeats step S104.

Specifically, the control unit 15 of the garbage collection device 10 notifies, via the communication unit 11 and the network 40, the control device 30 of the garbage collection site from which collection of the garbage is completed, every time the garbage is transported to the accumulation site. The control unit 33 of the control device 30 determines that the garbage is transported to the accumulation site after the control unit 33 acquires the notification from the garbage collection device 10 via the communication unit 31 and the network 40.

Step S105: When the control unit 33 determines that the garbage is transported to the accumulation site in step S104 (step S104—Yes), the control unit 33 determines whether collection of the garbage from all the garbage collection sites is completed.

Specifically, when the control unit 33 is notified from the garbage collection device 10 that collection of the garbage from all the garbage collection sites is completed in step S104, the control unit 33 determines that collection of the garbage from all the garbage collection sites is completed. When it is determined that collection of the garbage is completed (step S105—Yes), the process ends. On the other hand, when garbage collection sites of which the control unit 33 is not notified from the garbage collection device 10 in step S104 remain, the control unit 33 determines that collection of the garbage from the remaining garbage collection sites is not completed. When it is determined that collection of the garbage is not completed (step S105—No), the process returns to step S100 for the remaining garbage collection sites from which collection of the garbage is not completed (hereinafter simply referred to as "remaining garbage collection sites") as targets. When the process returns to step S100, the control unit 33 acquires the odor information on the remaining garbage collection sites again (step S100), redetermines the order in which the garbage is collected from the remaining garbage collection sites (step S101), redetermines the movement path based on the redetermined order (step S102), and causes the garbage collection device 10 to sequentially collect the garbage from the remaining garbage collection sites according to the redetermined order and the redetermined movement path (step S103). After that, steps S104 and S105 are executed again. Thus, steps S100 to S105 are repeatedly executed until collection of the garbage from all the garbage collection sites is completed.

As described above, the control device 30 according to the present embodiment acquires the odor information indicating the odor intensity of each garbage collection site detected by the odor sensor 20. The control device 30 determines the order in which the garbage is collected from each garbage collection site based on the odor information. Then, the control device 30 causes the garbage collection device 10 to sequentially collect the garbage from each garbage collection site according to the determined order.

With such a configuration, the order in which the garbage is collected is determined according to the odor intensity of each garbage collection site. Generally, when garbage with a strong odor intensity is left for a long period of time, there is a high possibility that users around such a garbage collection site feel uncomfortable. According to the present embodiment, a technique for collecting the garbage using the garbage collection device is improved in that the garbage is collected in the order in which the odor intensity of each garbage collection site is considered, for example, the garbage is collected in the order from a garbage collection site with a strong odor intensity, which leads to reduce a possibility that users feel uncomfortable.

Although the present disclosure has been described above based on the drawings and the embodiment, it should be noted that those skilled in the art may make various modifications and alterations thereto based on the present disclosure. It should be noted, therefore, that these modifications and alterations are within the scope of the present disclosure. For example, the functions included in the configurations, steps, etc. can be rearranged so as not to be logically inconsistent, and a plurality of configurations, steps, etc. can be combined into one or divided.

For example, in the above embodiment, the configuration and operation of the control device 30 may be distributed to a plurality of devices capable of communicating with each other. Furthermore, for example, an embodiment in which a part of or all of the components of the control device 30 are provided in the garbage collection device 10 is also possible.

Further, in the above embodiment, the case in which the garbage collection device 10 is an unmanned aerial vehicle such as a drone has been described. However, the garbage collection device 10 may be a vehicle such as a garbage collection vehicle. In such a case, for example, the accumulation site provided in the building such as a complex housing located in a garbage collection area can be adopted as a "garbage collection site" according to the present embodiment. Further, for example, the garbage disposal site can be adopted as an "accumulation site" according to the present embodiment.

An embodiment is also possible in which, for example, a general-purpose unmanned aerial vehicle or a computer functions as the garbage collection device 10 or the control device 30 in accordance with the above-described embodiment. Specifically, a program describing process contents for realizing each function of the garbage collection device 10 or the control device 30 according to the above-described embodiment is stored in the memory of a general-purpose unmanned aerial vehicle or a computer, and the program is read out and executed by the processor. Therefore, the present disclosure according to the present embodiment can also be realized as a program that can be executed by a processor or a non-transitory computer-readable medium that stores the program.

What is claimed is:

1. A method executed by a control device, the method comprising:
   acquiring odor information indicating an odor intensity of each of a plurality of garbage collection sites, the odor intensity being detected by an odor sensor;
   estimating a chronological change of the odor intensity of each of the garbage collection sites;
   determining an order in which garbage is collected from each of the garbage collection sites based on the odor intensity in the future of each of the garbage collection sites, the odor intensity being estimated based on the odor information, and the order being determined such that a sum of values obtained by integrating the odor intensity from a current time to a time at which a garbage collection device collects the garbage in each of the garbage collection sites is minimized; and
   causing the garbage collection device to sequentially collect the garbage from each of the garbage collection sites according to the order.

2. The method according to claim 1, further comprising determining a movement path of the garbage collection device for sequentially collecting the garbage from each of the garbage collection sites according to the order, wherein the control device causes the garbage collection device to sequentially collect the garbage from each of the garbage collection sites according to the order and the movement path.

3. The method according to claim 1, wherein the control device causes the garbage collection device to sequentially collect the garbage from each of the garbage collection sites according to the order such that the garbage is transported to an accumulation site every time the garbage is collected from a predetermined number of the garbage collection sites.

4. The method according to claim 3, wherein:
   the garbage collection device is an unmanned aerial vehicle;
   each of the garbage collection sites is provided on each balcony of a complex housing; and
   the accumulation site is provided in the complex housing.

5. The method according to claim 1, further comprising:
   when the garbage collection device transports garbage collected from part of the garbage collection sites to an accumulation site, acquiring odor information on remaining garbage collection sites again;
   redetermining the order in which the garbage is collected from each of the remaining garbage collection sites based on the odor information acquired again; and
   causing the garbage collection device to sequentially collect the garbage from the remaining garbage collection sites according to the redetermined order.

6. A control device comprising a control unit, wherein:
the control unit acquires odor information indicating an odor intensity of each of a plurality of garbage collection sites, the odor intensity being detected by an odor sensor;
the control unit estimates a chronological change of the odor intensity of each of the garbage collection sites;
the control unit determines an order in which garbage is collected from each of the garbage collection sites based on the odor intensity in the future of each of the garbage collection sites, the odor intensity being estimated based on the odor information, and the order being determined such that a sum of values obtained by integrating the odor intensity from a current time to a time at which a garbage collection device collects the garbage in each of the garbage collection sites is minimized; and
the control unit causes the garbage collection device to sequentially collect the garbage from each of the garbage collection sites according to the order.

7. The control device according to claim 6, wherein:
the control unit determines a movement path of the garbage collection device for sequentially collecting the garbage from each of the garbage collection sites according to the order; and
the control unit causes the garbage collection device to sequentially collect the garbage from each of the garbage collection sites according to the order and the movement path.

8. The control device according to claim 6, wherein the control unit causes the garbage collection device to sequentially collect the garbage from each of the garbage collection sites according to the order such that the garbage is transported to an accumulation site every time the garbage is collected from a predetermined number of the garbage collection sites.

9. The control device according to claim 8, wherein:
the garbage collection device is an unmanned aerial vehicle;
each of the garbage collection sites is provided on each balcony of a complex housing; and
the accumulation site is provided in the complex housing.

10. The control device according to claim 6, wherein:
when the garbage collection device transports garbage collected from part of the garbage collection sites to an accumulation site, the control unit acquires odor information on remaining garbage collection sites again;
the control unit redetermines the order in which garbage is collected from each of the remaining garbage collection sites based on the odor information acquired again; and the control unit causes the garbage collection device to sequentially collect the garbage from the remaining garbage collection sites according to the redetermined order.

11. A system comprising a control device and a garbage collection device that communicates with the control device, wherein:
the control device acquires odor information indicating an odor intensity of each of a plurality of garbage collection sites, the odor intensity being detected by an odor sensor;
the control device estimates a chronological change of the odor intensity of each of the garbage collection sites;
the control device determines an order in which garbage is collected from each of the garbage collection sites based on the odor intensity in the future of each of the garbage collection sites, the odor intensity being estimated based on the odor information, and the order being determined such that a sum of values obtained by integrating the odor intensity from a current time to a time at which the garbage collection device collects the garbage in each of the garbage collection sites is minimized; and
the garbage collection device sequentially collects the garbage from each of the garbage collection sites according to the order.

12. The system according to claim 11, wherein
the control device determines a movement path of the garbage collection device for sequentially collecting the garbage from each of the garbage collection sites according to the order; and
the garbage collection device sequentially collects the garbage from each of the garbage collection sites according to the order and the movement path.

13. The system according to claim 11, wherein the garbage collection device sequentially collects the garbage from each of the garbage collection sites according to the order such that the garbage is transported to an accumulation site every time the garbage is collected from a predetermined number of the garbage collection sites.

14. The system according to claim 13, wherein:
the garbage collection device is an unmanned aerial vehicle;
each of the garbage collection sites is provided on each balcony of a complex housing; and
the accumulation site is provided in the complex housing.

* * * * *